United States Patent
Sugiyama

(10) Patent No.: US 9,371,260 B2
(45) Date of Patent: Jun. 21, 2016

(54) METHOD FOR PRODUCING REFINED GLYCERIN ALKYL ETHER

(71) Applicant: KAO CORPORATION, Tokyo (JP)

(72) Inventor: Yukiteru Sugiyama, Narita (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/401,806

(22) PCT Filed: Apr. 24, 2013

(86) PCT No.: PCT/JP2013/062109
§ 371 (c)(1),
(2) Date: Nov. 17, 2014

(87) PCT Pub. No.: WO2013/172165
PCT Pub. Date: Nov. 21, 2013

(65) Prior Publication Data
US 2015/0126783 A1 May 7, 2015

(30) Foreign Application Priority Data
May 18, 2012 (JP) .................................. 2012-114957

(51) Int. Cl.
C07C 41/36 (2006.01)
(52) U.S. Cl.
CPC ...................................... *C07C 41/36* (2013.01)
(58) Field of Classification Search
CPC ...................................................... C07C 41/36
See application file for complete search history.

(56) References Cited

U.S. PATENT DOCUMENTS

| 3,742,069 A | 6/1973 | Hunter |
| 4,298,764 A | 11/1981 | Berkowitz |
| 2002/0035238 A1 | 3/2002 | Nakamura et al. |
| 2008/0176782 A1 | 7/2008 | Stephan et al. |
| 2008/0300429 A1 | 12/2008 | Sakanishi et al. |
| 2009/0239958 A1 | 9/2009 | Sakanishi et al. |

FOREIGN PATENT DOCUMENTS

| EP | 1785410 A1 | 5/2007 |
| JP | 87-58333 B2 | 12/1982 |
| JP | 3-227996 A | 10/1991 |
| JP | 5-117195 A | 5/1993 |

(Continued)

OTHER PUBLICATIONS

International Preliminary Report on Patentability and English translation of the Written Opinion of the International Searching Authority (Forms PCT/IB/338, PCT/IB/373 and PCT/ISA/237), mailed Nov. 27, 2014, for International Application No. PCT/JP2013/062109.

(Continued)

*Primary Examiner* — Rosalynd Keys
(74) *Attorney, Agent, or Firm* — Birch, Stewart, Kolasch & Birch, LLP

(57) ABSTRACT

Provided is a method for producing refined glycerin alkyl ether at a high recovery rate by removing glycerin from a mixture containing glycerin and glycerin alkyl ether. A method for producing refined glycerin alkyl ether comprising the following steps (1) and (2): step (1): bringing a mixture containing glycerin and glycerin alkyl ether into contact with a cation exchange resin; step (2): bringing the cation exchange resin into contact with a solvent having an SP value of from 20.5 to 34 $(MPa)^{1/2}$ to obtain an eluate.

19 Claims, 1 Drawing Sheet

(56) References Cited

FOREIGN PATENT DOCUMENTS

| | | | |
|---|---|---|---|
| JP | 5-310625 A | 11/1993 |
| JP | 8-143513 A | 6/1996 |
| JP | 9-100243 A | 4/1997 |
| JP | 2001-114720 A | 4/2001 |
| JP | 2005-281216 A | 10/2005 |
| JP | 2007-9167 A | 1/2007 |
| JP | 2007-9187 A | 1/2007 |
| JP | 2008-534652 A | 8/2008 |
| JP | 2009-227583 A | 10/2009 |
| JP | 2010-100531 A | 5/2010 |
| JP | 2012-106957 A | 6/2012 |
| JP | 2013-151463 A | 8/2013 |
| WO | 2006/025226 A1 | 3/2006 |
| WO | WO 2006/025226 A1 | 3/2006 |

OTHER PUBLICATIONS

International Search Report issued in PCT/JP2013/062109, dated Jul. 2, 2013.
Extended European Search Report dated Dec. 1, 2015, for European Application No. 13790664.0.

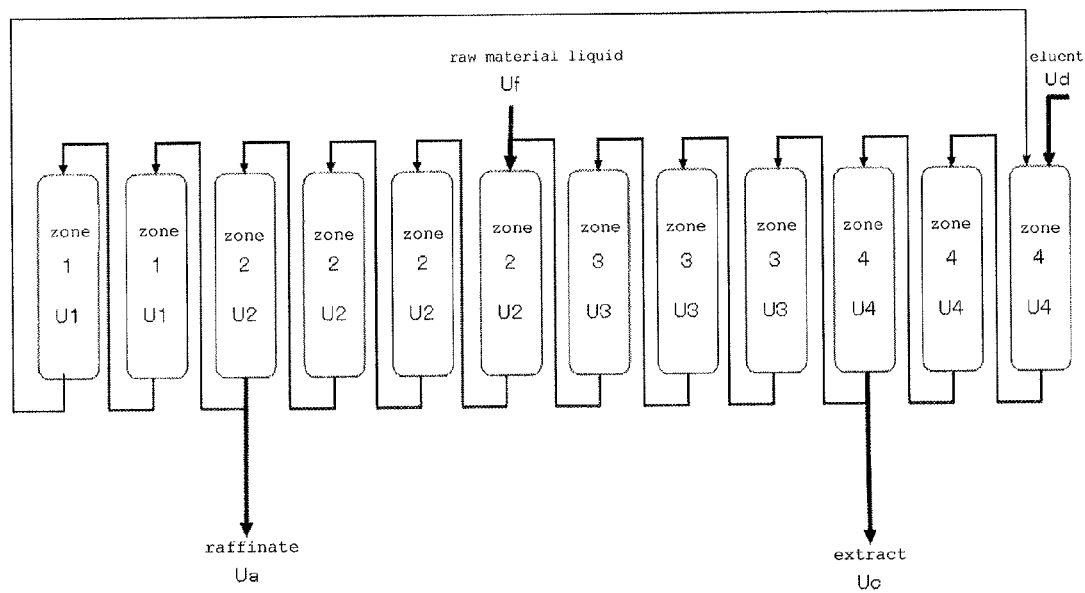

METHOD FOR PRODUCING REFINED GLYCERIN ALKYL ETHER

FIELD OF THE INVENTION

The present invention relates to a method for producing refined glycerin alkyl ether.

BACKGROUND OF THE INVENTION

Glycerin-based surfactants such as glycerin alkyl ether are utilized in various fields, such as foods, cosmetics, medicaments, and the like, for their excellent functions as a nonionic surfactant.

Known producing methods of glycerin alkyl ether include, for example, a ring-opening polymerization of glycidol with alcohol in the presence of a basic catalyst, addition of alkyl glycidyl ether to polyglycerin (Patent Document 1), addition of olefin to polyglycerin (Patent Document 2), and the like.

As a purification method of the reaction product, a chromatographic separation is known. For example, a method to bring crude alkyl glucoside containing higher alcohol as an impurity into contact with silica gel or synthetic adsorbent, followed by separating the higher alcohol and alkyl glucoside by a simulated moving bed chromatography (Patent Document 3), a method to adsorb a mixture containing at least two kinds of higher aliphatic compounds selected from higher aliphatic hydrocarbon, higher fatty acid complete ester, higher aliphatic alcohol, higher fatty acid partial ester, and higher aliphatic nonionic surfactant onto a column filled with silica gel, followed by eluting the component sequentially from more hydrophobic higher aliphatic compound by passing a plurality of organic solvents with different hydrophobicity sequentially from more hydrophobic solvent (Patent Document 4), a method to remove a low molecular weight component from a polyglycerin mixture using a particular ion exchange resin and water (Patent Document 5), and the like have been proposed.

CITATION LIST

Patent Document

Patent Document 1: JP2005-281216A
Patent Document 2: JP2008-534652T
Patent Document 3: JPH03-227996A
Patent Document 4: JPH09-100243A
Patent Document 5: JPH08-143513A

SUMMARY OF THE INVENTION

The present invention provides a method for producing refined glycerin alkyl ether comprising the following steps (1) and (2):

step (1) to bring a mixture containing glycerin and glycerin alkyl ether into contact with a cation exchange resin:

step (2) to bring the cation exchange resin into contact with a solvent having an SP value of from 20.5 to 34 $(MPa)^{1/2}$ to obtain an eluate.

BRIEF DESCRIPTION OF THE DRAWINGS

FIG. 1 is a schematic diagram showing an example of the simulated moving bed separation apparatus.

DETAILED DESCRIPTION OF THE INVENTION

In the industrial production of glycerin alkyl ether, the product contains monoglycerin alkyl ether and polyglycerin alkyl ether having a different degree of polymerization of glycerin. The product also contains glycerin monoalkyl ether and glycerin polyalkyl ether having a different number of alkyl groups. In addition, monoglycerin and polyglycerin having a different degree of polymerization of glycerin remain as unreacted glycerin.

Note that both of monoglycerin and polyglycerin are represented by "glycerin" in the present specification. In addition, monoglycerin monoalkyl ether and polyglycerin monoalkyl ether, and monoglycerin polyalkyl ether and polyglycerin polyalkyl ether are collectively represented by "glycerin alkyl ether". Similar nomenclature is adopted for the compounds having a glycerol residue originated from glycerin.

Among the above-mentioned methods for producing glycerin alkyl ether, addition of alkyl glycidyl ether or olefin to glycerin is advantageous because of easy control of the degree of polymerization of glycerin. However, removal of unreacted glycerin after the reaction is inevitable, because a large excess of glycerin is required in order to suppress the formation of polyalkyl ether body. Although glycerin may be removed by distillation in this case, glycerin is hard to be removed due to its high boiling temperature.

Although chromatographic purification may be conceivable as described in the above-mentioned Patent Document 3 and Patent Document 4, Patent Document 3 and Patent Document 4 aim at separation of alkyl glucoside and unreacted alcohol and separation of at least two kinds of higher aliphatic compounds, respectively. Patent Document 5 discloses separation of low molecular weight reactants from polyglycerin mixture. Therefore, there have been no reports regarding separation of glycerin alkyl ether and glycerin. Findings in the conventional chromatographic separation are not necessarily applicable to the purification of glycerin alkyl ether as they are, because chromatographic separation is greatly affected generally not only by the composition of the mixture to be separated, but also by the kind of adsorbent and solvent to be used, substrate concentration of the mixture to be separated, temperature, and the like.

Accordingly, the present invention relates to providing a method for producing refined glycerin alkyl ether in a high yield by removing glycerin from a mixture containing glycerin and glycerin alkyl ether.

As a result of extensive investigation, the present inventor found that refined glycerin alkyl ether may be produced in a high yield by bringing a mixture containing glycerin and glycerin alkyl ether into contact with a cation exchange resin and then bringing the cation exchange resin into contact with a specific solvent to obtain an eluate.

According to the present invention, refined glycerin alkyl ether with a high purity may be produced from a mixture containing glycerin and glycerin alkyl ether in a high yield by a simple operation.

Hereinafter the steps (1) and (2) will be described in detail.

Step (1)

In step (1), a mixture containing glycerin and glycerin alkyl ether is brought into contact with a cation exchange resin. The above-mentioned mixture contains glycerin and glycerin alkyl ether, the former being easily adsorbed, whereas the latter being hard to be adsorbed by the cation exchange resin.

<A Mixture Containing Glycerin and Glycerin Alkyl Ether>

The above-mentioned mixture used in the present invention contains glycerin and glycerin alkyl ether, the latter being represented by the following formula (1).

$$R^1O-(C_3H_6O_2)_nR^2 \quad (1)$$

(wherein $R^1$ represents a hydrocarbon group having 8 to 22 carbon atoms, $R^2$ represents hydrogen atom or a hydrocarbon group having 8 to 22 carbon atoms, $(C_3H_6O_2)_n$ represents glycerin moiety, n represents the mass average degree of polymerization of the glycerol residue in the glycerin moiety and a number of from 1 to 10.)

In addition, the above-mentioned mixture may contain glycerin alkyl ether having three or more alkyl groups.

The number of carbon atoms of the hydrocarbon group included in $R^1$ and $R^2$ is 8 or more, preferably 10 or more, and more preferably 12 or more, from the viewpoint of production efficiency, high purity, and high yield of glycerin alkyl ether, and from the viewpoint of cleaning performance of glycerin alkyl ether, and is 22 or less, preferably 18 or less, and more preferably 14 or less, from the viewpoint of production efficiency, high purity, and high yield, and from the viewpoint of property of glycerin alkyl ether. The range of the number of carbon atoms of the hydrocarbon group is preferably from 8 to 22, more preferably from 10 to 18, even more preferably from 12 to 14.

Although the hydrocarbon group in $R^1$ and $R^2$ may be any of saturated and unsaturated or linear, branched chain and cyclic, it is preferably saturated or unsaturated linear or branched chain hydrocarbon group, more preferably saturated or unsaturated linear hydrocarbon group, even more preferably saturated linear hydrocarbon group, from the viewpoint of production efficiency, high purity, and high yield, as well as from the viewpoint of cleaning performance and property of glycerin alkyl ether.

In general formula (1), n is from 1 to 10, preferably from 1 to 7 from the viewpoint of production efficiency, high purity, and high yield of glycerin alkyl ether and from the viewpoint of the cleaning power of glycerin alkyl ether when used as a detergent.

The specific structure of the glycerin moiety represented by $(C_3H_6O_2)_n$ includes those having the linear portion with one or more structures selected from the following formula (1-1) to (1-3) and those having the branched portion with a structure selected from the following formula (1-4) to (1-6) if the branched portion is included,

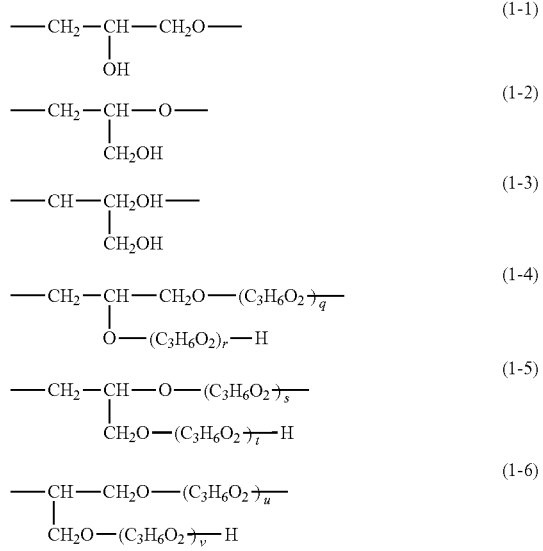

(wherein q, r, s, t, u, and v mutually independently represent an integer of 1 or more.)

In the general formula (1-4) to (1-6), q, r, s, t, u, and v are preferably mutually independently from 1 to 8, more preferably from 1 to 3, even more preferably 1 or 2, from the viewpoint of production efficiency, high purity, and high yield of glycerin alkyl ether and from the viewpoint of the cleaning power of glycerin alkyl ether when used as a detergent.

The above-mentioned mixture to be used in the present invention may contain a solvent. Although the solvents are not specifically limited, the same solvent as used in step (2) described later is preferable, from the viewpoint of production efficiency, high purity, and high yield of refined glycerin alkyl ether. The solvent will be described in more detail in step (2).

Content of the solvent in the above-mentioned mixture is preferably 1% by mass or more, more preferably 10% by mass or more, even more preferably 15% by mass or more, from the viewpoint of production efficiency, high purity, and high yield of refined glycerin alkyl ether, and is preferably 70% by mass or less, more preferably 60% by mass or less, even more preferably 50% by mass or less, from the viewpoint of production efficiency, high purity, and high yield of refined glycerin alkyl ether. The range of the content of the solvent in the above-mentioned mixture is preferably from 1 to 70% by mass, more preferably from 10 to 60% by mass, even more preferably from 15 to 50% by mass.

The reaction product obtained by a known synthetic method to form glycerin alkyl ether may be used as the above-mentioned mixture, and no particular limit is imposed on the synthetic method. The product directly synthesized may be used as it is, otherwise the concentration of the product may be adjusted by adding a solvent and the like after the synthesis. Among them, the reaction product obtained by a synthetic method to form glycerin alkyl ether using glycerin as the raw material may be preferably used. Examples of such reaction products include the reaction product of glycerin and alkyl glycidyl ether, the reaction product of glycerin and olefin, and the like. Among them, the reaction product of glycerin and alkyl glycidyl ether is preferable.

The preferred compositions of glycerin alkyl ether contained in the mixture include the following, from the viewpoint of production efficiency, high purity, and high yield of refined glycerin alkyl ether and the cleaning power of glycerin alkyl ether when used as a detergent.

Content of the compound with n=1 in the general formula (1) is preferably from 0.1 to 2% by mass, more preferably from 0.2 to 1% by mass, even more preferably from 0.3 to 0.5% by mass.

Content of the compound with n=2 in the general formula (1) is preferably from 0.1 to 25 mass %, more preferably from 0.1 to 20% by mass.

Content of the compound with n=3 in the general formula (1) is preferably from 0.1 to 25% by mass, more preferably from 1 to 20% by mass.

Content of the compound with n=4 in the general formula (1) is preferably from 0.1 to 25% by mass, more preferably from 0.1 to 20% by mass.

Content of the compound with n=5 in the general formula (1) is preferably from 0.1 to 15% by mass, more preferably from 1 to 10% by mass.

Content of the compound with n=6 or more in the general formula (1) is preferably from 0.1 to 10% by mass, more preferably from 0.2 to 5% by mass, even more preferably from 0.3 to 4% by mass.

Total content of glycerin alkyl ether in the mixture is preferably 5% by mass or more, more preferably 10% by mass or more, even more preferably 15% by mass or more, from the viewpoint of production efficiency and high purity of refined glycerin alkyl ether, and is preferably 60% by mass or less, more preferably 50% by mass or less, even more preferably 40% by mass or less, from the viewpoint of high yield of refined glycerin alkyl ether. The range of the total content of glycerin alkyl ether in the mixture is preferably from 5 to 60% by mass, more preferably from 10 to 50% by mass, even more preferably from 15 to 40% by mass.

The mixture may contain glycerin polyalkyl ether (hereinafter referred to also as "polyalkyl ether body"). Total content of polyalkyl ether body in the mixture is preferably 10% by mass or less, more preferably 8% by mass or less, even more preferably 5% by mass or less, from the viewpoint of production efficiency, high purity, and high yield of refined glycerin alkyl ether and from the viewpoint of the cleaning power of glycerin alkyl ether when used as a detergent. Although the lower limit of the total content of polyalkyl ether body (component 5 in Table 1 of Example described later) in the mixture may be 0% by mass, it is preferably 0.001% by mass, more preferably 0.01% by mass, from the viewpoint of production efficiency of refined glycerin alkyl ether.

Although cyclic body of glycerin and glycerin with the degree of polymerization of 6 or more may be contained in the mixture, total content of glycerin with the degree of polymerization of 6 or more and cyclic body of glycerin (component 2 in Table 1 of Example described later) in the mixture is preferably 20% by mass or less, more preferably 15% by mass or less, more preferably 10% by mass or less, even more preferably 5% by mass or less, from the viewpoint of production efficiency, high purity, and high yield of refined glycerin alkyl ether and the cleaning power of glycerin alkyl ether when used as a detergent. Although the lower limit of the total content of glycerin with the degree of polymerization of 6 or more and cyclic body of glycerin in the mixture may be 0% by mass, it is preferably 0.001% by mass, more preferably 0.01% by mass, even more preferably 0.1% by mass, from the viewpoint of production efficiency of refined glycerin alkyl ether.

Although the mixture may contain monoglycerin, content of monoglycerin in the mixture is preferably 20% by mass or less, more preferably 15% by mass or less, more preferably 10% by mass or less, even more preferably 1% by mass or less, and the most preferably the mixture does not contain monoglycerin at all, from the viewpoint of production efficiency, high purity, and high yield of refined glycerin alkyl ether.

Although the reaction condition of glycerin and alkyl glycidyl ether or olefin may be determined as needed, for example, in the case of the reaction of glycerin and alkyl glycidyl ether, feed amount of glycerin relative to one mole of alkyl glycidyl ether is preferably 1 mole or more, more preferably 1.2 moles or more, even more preferably 2 moles or more, from the viewpoint of suppressing the formation of polyalkyl ether body, and is preferably 10 moles or less, more preferably 7 moles or less, even more preferably 6 moles or less, from the viewpoint of reducing the amount of glycerin to be used. The range of feed amount of glycerin relative to one mole of alkyl glycidyl ether is preferably from 1 to 10 moles, more preferably from 1.2 to 7 moles, even more preferably from 2 to 6 moles.

Reaction of glycerin and alkyl glycidyl ether may be carried out in the presence of basic catalyst, which includes, for example, sodium hydroxide, potassium hydroxide, sodium carbonate, potassium carbonate, and the like.

The reaction temperature is preferably 40° C. or higher, more preferably 100° C. or higher, more preferably 150° C. or higher, even more preferably 180° C. or higher, from the viewpoint of increasing the reaction rate and shortening the process time, and is preferably 220° C. or lower, more preferably 210° C. or lower, even more preferably 200° C. or lower, from the viewpoint of preventing coloration of the addition product and suppressing odor. The range of the reaction temperature is preferably from 40 to 220° C., more preferably from 100 to 210° C., more preferably from 150 to 200° C., even more preferably from 180 to 200° C.

Alkyl glycidyl ether and glycerin may be obtained by known production method. Alkyl glycidyl ether may be obtained by reacting alcohols and α-epihalohydrin, followed by ring closing by alkali treatment, as described in Japanese Patent No. 3544134. Glycerin may be obtained by known method such as the dehydrative condensation reaction of glycerin using an alkali catalyst.

<Cation Exchange Resin>

Base materials of the cation exchange resin include, for example, crosslinked polystyrene such as styrene-divinylbenzene, (co)polymer having a (meth)acrylic acid monomer unit, and the like, in which crosslinked polystyrene is preferable. As the base structure, gel-type and porous-type are exemplified, in which gel-type is preferable from the viewpoint of production efficiency, high purity, and high yield of refined glycerin alkyl ether. Form of the resin includes powder, sphere, fiber, membrane, and the like, in which spheres are preferable from the viewpoint of production efficiency, high purity, and high yield of refined glycerin alkyl ether.

Although the average particle diameter ($d_{50}$) of the cation exchange resin is not particularly limited, it is preferably 100 μm or more, more preferably 150 μm or more, more preferably 200 nm or more, more preferably 250 μm or more, even more preferably 300 μm or more, from the viewpoint of production efficiency and high yield of refined glycerin alkyl ether, and is preferably 900 μm or less, more preferably 550 μm or less, more preferably 500 μm or less, more preferably 450 μm or less, even more preferably 400 μm or less, from the viewpoint of production efficiency, high purity, and high yield of refined glycerin alkyl ether. The range of the average particle diameter ($d_{50}$) is preferably from 100 to 900 μm, more preferably from 150 to 550 μm, more preferably from 200 to 500 μm, more preferably from 250 μm to 450 μm, even more preferably from 300 to 400 μm. "Average particle diameter" herein means the median diameter ($d_{50}$) derived from the particle size distribution of the cation exchange resin on the number basis measured by laser diffraction scattering method.

The cation exchange resin includes strong acid cation exchange resin having a sulfonic acid group and the like as the exchange group and weak acid cation exchange resin having a carboxylic group, phosphoric acid group, and the like as the exchange group, in which strong acid cation exchange resin is preferable from the viewpoint of production efficiency, high purity, and high yield of refined glycerin alkyl ether.

Although the degree of crosslinking of the cation exchange resin is not particularly limited, it is preferably 2% or more, more preferably 4% or more, even more preferably 6% or more, from the viewpoint of production efficiency, high purity, and high yield of refined glycerin alkyl ether, and is preferably 20% or less, more preferably 16% or less, even more preferably 10% or less, from the similar viewpoint to the above. The range of the degree of crosslinking is preferably from 2 to 20%, more preferably from 4 to 16%, even more preferably from 6 to 10%.

Although the exchange capacity of the cation exchange resin is not particularly limited, it is preferably 0.5 meq/mL or more, more preferably 1.0 meq/mL or more, even more preferably 1.3 meq/mL or more, from the viewpoint of production efficiency, high purity, and high yield of refined glycerin alkyl ether, and is preferably 3 meq/mL or less, more preferably 2.5 meq/mL or less, even more preferably 1.8 meq/mL or less, from the similar viewpoint to the above. The range of the exchange capacity is preferably from 0.5 meq/mL to 3.0 meq/mL, more preferably from 1.0 meq/mL to 2.5 meq/mL, even more preferably from 1.3 meq/mL to 1.8 meq/mL.

The preferred cation exchange resin includes alkali metal type cation exchange resin and alkali earth metal type cation exchange resin having alkali metal ion and alkali earth metal ion, respectively, as the counter ion, from the viewpoint of production efficiency, high purity, and high yield of refined glycerin alkyl ether. Examples of the alkali metal type cation exchange resin include sodium type cation exchange resin and potassium type cation exchange resin. Examples of the alkali earth metal type cation exchange resin include calcium type cation exchange resin. Among them, alkali metal type cation exchange resin is preferable, sodium type cation exchange resin being more preferable.

The cation exchange resin of alkali metal type or alkali earth metal type may be prepared by converting the hydrogen ion of hydrogen type (H type) cation exchange resin to alkali metal ion or alkali earth metal ion. Conventional preparation method may be adopted, including, for example, a method to bring an aqueous solution of alkali metal salt, such as sodium chloride, potassium chloride, and the like or an aqueous solution of alkali earth metal salt, such as calcium chloride and the like into contact with a hydrogen type cation exchange resin, followed by washing the cation exchange resin after contacting treatment with ion exchange water.

Commercial products may be used as the cation exchange resin of alkali metal type or alkali earth metal type. Such examples include alkali metal type cation exchange resin such as DIAION UBK530, DIAION UBK08, DIAION PK220, DIAION SK104 (produced by Mitsubishi Chemical Corporation) and AMBERLITE CR1310Na (produced by the Dow Chemical Company), and alkali earth metal type cation exchange resin such as DIAION UBK535 (produced by Mitsubishi Chemical Corporation) and AMBERLITE CR1310Ca (produced by the Dow Chemical Company).

<Contact Treatment>

Contact treatment with the cation exchange resin may be performed using any of batch method and continuous method. The cation exchange resin may be dispersed in the mixture solution and then be filtered to separate the cation exchange resin. In the industrial process, a fixed bed method may be adopted in which the above-mentioned mixture is passed into a column filled with the cation exchange resin to perform the contact treatment.

As for the contact condition in the fixed bed method, superficial velocity (SV) is preferably 0.5/hr or more, more preferably 2/hr or more, from the viewpoint of production efficiency, high purity, and high yield of refined glycerin alkyl ether, and is preferably 10/hr or less, more preferably 4/hr or less, from the similar viewpoint to the above. The range of SV is preferably from 0.5 to 10/hr, more preferably from 2 to 4/hr. Superficial linear velocity is preferably 0.2 m/h or more, more preferably 1 m/h or more, from the similar viewpoint to the above, and is preferably 4.9 m/h or less, more preferably 2 m/h or less, from the similar viewpoint to the above. The range of the superficial linear velocity is preferably from 0.2 to 4.9 m/h, more preferably from 1 to 2 m/h. Contact temperature is preferably 30° C. or higher, more preferably 40° C. or higher, even more preferably 50° C. or higher, from the similar viewpoint to the above, and is preferably 90° C. or lower, more preferably 80° C. or lower, even more preferably 65° C. or lower, from the similar viewpoint to the above. The range of the contact temperature is preferably from 30 to 90° C., more preferably from 40 to 80° C., even more preferably from 50 to 65° C.

As for the amount of the cation exchange resin to be used, volume ratio (v/v) of the above-mentioned mixture to the cation exchange resin is preferably 0.005 or more, more preferably 0.01 or more, even more preferably 0.03 or more, from the viewpoint of production efficiency of refined glycerin alkyl ether, and is preferably 0.5 or less, more preferably 0.1 or less, even more preferably 0.05 or less, from the viewpoint of production efficiency, high purity, and high yield of refined glycerin alkyl ether. The range of the volume ratio (v/v) of the above-mentioned mixture to the cation exchange resin is preferably from 0.005 to 0.5, more preferably from 0.01 to 0.1, even more preferably from 0.03 to 0.05.

<Recovery>

In the fixed bed method, the eluted fraction which was not adsorbed by the cation exchange resin is recovered.

[Step (2)]

In step (2), the cation exchange resin after step (1) is brought into contact with a solvent having an SP value of from 20.5 to 34 $(MPa)^{1/2}$ to obtain an eluate. The difference of adsorption performance of the cation exchange resin to glycerin and glycerin alkyl ether becomes significant by using such a solvent as the eluent. Accordingly, the eluate having a decreased concentration of glycerin and an increased concentration of glycerin alkyl ether may be obtained. "Eluent" herein means a solvent to separate the substance adsorbed by the cation exchange resin from the resin. "Eluate" herein means a solution containing the adsorbed substance which has been separated from the cation exchange resin. A fraction rich in glycerin alkyl ether is obtained from the first half of the eluate and a fraction rich in glycerin is obtained from the second half of the eluate.

Solvent

In the present invention, a solvent having an SP value of from 20.5 to 34 $(MPa)^{1/2}$ is used. The SP value is preferably 23 $(MPa)^{1/2}$ or more, more preferably 24 $(MPa)^{1/2}$ or more, more preferably 25 $(MPa)^{1/2}$ or more, even more preferably 26 $(MPa)^{1/2}$ or more, from the viewpoint of production efficiency, high purity, and high yield of refined glycerin alkyl ether and from the viewpoint that both of the raw material liquid and the separated liquid are soluble, and is preferably 33 $(MPa)^{1/2}$ or less, more preferably 32 $(MPa)^{1/2}$ or less, more preferably 31 $(MPa)^{1/2}$ or less, even more preferably 30 $(MPa)^{1/2}$ or less, from the similar viewpoint to the above. The range of the SP value of the solvent is preferably from 23 to 33 $(MPa)^{1/2}$, more preferably from 24 to 32 $(MPa)^{1/2}$, more preferably from 25 to 31 $(MPa)^{1/2}$, even more preferably from 26 to 30 $(MPa)^{1/2}$. "SP value" herein means the solubility parameter, which is shown by J. Brandrup, "Polymer Handbook 4th", John Wiley & Sons, Inc., 1999, VII 688-694 or may be calculated using the parameter shown by J. Brandrup, "Polymer Handbook 4th", VII 685-686 according to Fedors' method.

The solvent may contain water. Water content of the solvent is preferably 5% by mass or less, more preferably 3% by mass or less, even more preferably 1% by mass or less, from the viewpoint of prevention of foaming. Although the lower limit of the water content of the solvent may be 0% by mass, it is preferably 0.001% by mass, more preferably 0.01% by mass, from the viewpoint of production efficiency of refined glycerin alkyl ether. Water content of the solvent is preferably from 0 to 5% by mass, more preferably from 0.001 to 3% by mass, even more preferably from 0.01 to 1% by mass. Water content of the solvent may be measured by Karl Fischer method, the detail of which will be described in Example.

In the present invention, it is preferable to use the solvent having a boiling temperature at atmospheric pressure of from 40 to 95° C. among those having the above-mentioned range of SP value. Boiling temperature of such solvent is preferably from 50 to 90° C., more preferably from 55 to 85° C., even more preferably from 60 to 80° C., from the viewpoint of production efficiency, high purity, and high yield of refined glycerin alkyl ether, as well as the efficiency of solvent removal.

Specific examples of the solvents used in the present invention include methanol (29.7), ethanol (26.7), propanol (24.6), and the like (numbers in parentheses represent SP value). They may be used solely or in combination of two or more kinds.

When two or more kinds of the solvent are mixed, the solvent having an SP value outside of the range of from 20.5 to 34 $(MPa)^{1/2}$ may be used in combination as needed so that the SP value of the mixed solvent falls into the above range. Examples of such solvent include hexane (14.7), acetone (20.1), acetic acid (21.5), isopropyl alcohol (23.6), and the like. When two or more kinds of the solvent are mixed, the SP value of the mixed solvent is the sum of the SP value of each solvent multiplied by the volume fraction of each solvent.

<Contact Treatment>

Contact treatment of the cation exchange resin with the solvent may be performed using any of batch method and continuous method similarly to step (1) mentioned above. A fixed bed method and the like may be preferably adopted.

As for the contact condition, superficial velocity (SV) is preferably 0.5/hr or more, more preferably 2/hr or more, from the viewpoint of production efficiency, high purity, and high yield of refined glycerin alkyl ether, and is preferably 10/hr or less, more preferably 4/hr or less, from the similar viewpoint to the above. The range of SV is preferably from 0.5 to 10/hr, more preferably from 2 to 4/hr. Superficial linear velocity is preferably 0.2 m/h or more, more preferably 1 m/h or more, from the similar viewpoint to the above, and is preferably 4.9 m/h or less, more preferably 2 m/h or less, from the similar viewpoint to the above. The range of the superficial linear velocity is preferably from 0.2 to 4.9 m/h, more preferably from 1 to 2 m/h. Contact temperature is preferably 30° C. or higher, more preferably 40° C. or higher, even more preferably 50° C. or higher, from the similar viewpoint to the above, and is preferably 90° C. or lower, more preferably 80° C. or lower, even more preferably 65° C. or lower, from the similar viewpoint to the above. The range of the contact temperature is preferably from 30 to 90° C., more preferably from 40 to 80° C., even more preferably from 50 to 65° C.

Amount of the solvent used relative to the above-mentioned mixture is preferably 2 or more, more preferably 5 or more, more preferably 10 or more, even more preferably 20 or more, from the viewpoint of high purity and high yield of refined glycerin alkyl ether, and is preferably 200 or less, more preferably 180 or less, more preferably 160 or less, even more preferably 150 or less relative to the above-mentioned mixture, from the viewpoint of production efficiency of refined glycerin alkyl ether and efficiency of solvent removal. The range of the amount of the solvent used relative to the above-mentioned mixture is preferably from 2 to 200, more preferably from 5 to 180, more preferably from 10 to 160, even more preferably from 20 to 150.

In the present invention, the above-mentioned steps (1) and (2) may be performed according to the simulated moving bed technique. "Simulated moving bed technique" herein means a chromatographic separation technique which exerts the similar function to the moving bed technique in which the cation exchange resin moves, without actually moving the resin. In this technique, valves are provided at the top and bottom of each of a plurality of the packed bed columns filled with the cation exchange resin which are connected together in series and endlessly. Predetermined positions calculated from basic properties obtained from the fixed bed experimentation are set as the feeding port of the raw material liquid, the feeding port of the eluent, the discharge port of the raffinate fraction which is poorly adsorbed by the cation exchange resin, and the discharge port of the extract fraction which is readily adsorbed by the cation exchange resin. These positions are moved sequentially downstream in the circulation direction in the system with a certain switching time from column to column, keeping the constant relative position of each feeding port and discharge port provided on the packed columns. Chromatographic separation apparatuses based on such simulated moving bed technique are known and commercially available for the use in the present invention. Examples include New JO type chromatographic separation apparatus manufactured by Organo Corporation and the improved simulated moving bed chromatographic separation apparatus manufactured by Nippon Rensui Co. Note that the components of the above-mentioned mixture as the raw material liquid, the cation exchange resin and the solvent are as described above.

Since glycerin alkyl ether is more poorly adsorbed by the cation exchange resin than glycerin, moving velocity of glycerin alkyl ether in the packed bed columns is larger than that of glycerin. Therefore, the ratio (Ud/Uf) of the feeding velocity of the solvent as the eluent (Ud) to the feeding velocity of the above-mentioned mixture as the raw material liquid (Uf) is preferably 2 or more, more preferably 3 or more, more preferably 3.5 or more, more preferably 4 or more, even more preferably 5 or more, from the viewpoint of production efficiency, high purity, and high yield of refined glycerin alkyl ether, and is preferably 40 or less, more preferably 25 or less, more preferably 20 or less, more preferably 18 or less, even more preferably 15 or less, from the viewpoint of production efficiency of refined glycerin alkyl ether and efficiency of solvent removal. The range of Ud/Uf is preferably from 2 to 40, more preferably from 3 to 25, more preferably from 3.5 to 20, more preferably from 4 to 18, even more preferably from 5 to 15.

The feeding velocity relative to the total column length (Uf) is preferably 0.001 m/m/h or more, more preferably 0.005 m/m/h or more, even more preferably 0.01 m/m/h or more, from the viewpoint of production efficiency, high purity, and high yield of refined glycerin alkyl ether, and is preferably 0.1 m/m/h or less, more preferably 0.05 m/m/h or less, even more preferably 0.03 m/m/h or less, from the similar viewpoint to the above. The range of Uf is preferably from 0.001 to 0.1 m/m/h, more preferably from 0.005 to 0.05 m/m/h, even more preferably from 0.01 to 0.03 m/m/h.

The total number of the columns is preferably from 8 to 16, more preferably from 10 to 14, even more preferably 12, from the viewpoint of production efficiency, high purity, and high yield of refined glycerin alkyl ether. If the packed bed columns are composed of 4 zones, the number of the columns in each zone is preferably from 2 to 4 for zone 1, from 3 to 4 for zone 2, from 3 to 4 for zone 3, and from 3 to 4 for zone 4, more preferably 2 for zone 1, 4 for zone 2, 3 for zone 3, and 3 for zone 4.

Contact temperature is preferably from 30 to 90° C., more preferably from 40 to 80° C., even more preferably from 50 to 65° C.

In the simulated moving bed technique, raffinate fraction is recovered since the extract fraction is rich in glycerin and the raffinate fraction is rich in glycerin alkyl ether.

After the above-mentioned step (2), the process may include a step to remove the solvent in the eluate obtained in step (2). In order to remove the solvent, common techniques such as reduced pressure concentration and the like may be used. Common apparatuses such as a distillation column, multieffect evaporator, and the like may be used as the apparatus. Among them, it is preferable to use a multieffect evaporator with the improved heat efficiency.

Although the resultant eluate may contain water, water content of the eluate is preferably 5% by mass or less, more preferably 3% by mass or less, even more preferably 1% by mass or less, from the viewpoint of prevention of foaming at the solvent removal step. Although the lower limit of the water content of the eluate may be 0% by mass, it is preferably 0.001% by mass, more preferably 0.01% by mass, from the viewpoint of production efficiency of refined glycerin alkyl ether. Water content of the above-mentioned eluate is preferably from 0 to 5% by mass, more preferably from 0.001 to 3% by mass, even more preferably from 0.01 to 1% by mass. Water content of the eluate may be measured by Karl Fischer method.

Refined glycerin alkyl ether can be recovered in such a high yield as preferably 80% or more, more preferably 85% or more, more preferably 90% or more, even more preferably 95% or more. The upper limit of the yield is not particularly limited and may be 100%.

Purity of refined glycerin alkyl ether obtained after removal of the solvent is preferably 46% or more, more preferably 50% or more, more preferably 70% or more, more preferably 75% or more, more preferably 85% or more, even more preferably 90% or more. Although the upper limit of the purity is not particularly limited and may be 100%, it is preferably 99.8% or less, more preferably 99.5% or less, more preferably 99% or less, more preferably 98.5% or less, even more preferably 98% or less, from the viewpoint of production efficiency and high yield of refined glycerin alkyl ether. The range of the purity of refined glycerin alkyl ether is preferably from 46 to 100%, more preferably from 50 to 99.8%, more preferably from 70 to 99.5%, more preferably from 75 to 99%, more preferably from 85 to 98.5%, even more preferably from 90 to 98%.

Refined glycerin alkyl ether obtained according to the production method of the present invention is useful as a non-ionic surfactant and may be used, for example, for the purpose of emulsification, solubilization, dispersion, cleaning, foaming, defoaming, penetration, antibacterial agent, and the like.

The present invention further discloses the following production method regarding to the above-mentioned embodiments.

(1)
A method for producing refined glycerin alkyl ether comprising the following steps (1) and (2):
Step (1): A step to bring a mixture containing glycerin and glycerin alkyl ether into contact with a cation exchange resin;
Step (2): A step to bring the cation exchange resin into contact with a solvent having an SP value of from 20.5 to 34 $(MPa)^{1/2}$ to obtain an eluate.

(2)
The method for producing refined glycerin alkyl ether described in (1), wherein the average particle diameter of the cation exchange resin is preferably from 100 to 900 μm, more preferably from 150 to 550 μm, more preferably from 200 to 500 μm, more preferably from 250 μm to 450 μm, even more preferably from 300 to 400 μm.

(3)
The method for producing refined glycerin alkyl ether described in (1), wherein the average particle diameter of the cation exchange resin is preferably 100 μm or more, more preferably 150 μm or more, more preferably 200 μm or more, more preferably 250 μm or more, even more preferably 300 μm or more, and is preferably 900 μm or less, more preferably 550 μm or less, more preferably 500 μm or less, more preferably 450 μm or less, even more preferably 400 μm or less.

(4)
The method for producing refined glycerin alkyl ether described in any one of (1) to (3), wherein the cation exchange resin is at least one selected from alkali metal type and alkali earth metal type.

(5) The method for producing refined glycerin alkyl ether described in any one of (1) to (4), wherein the cation exchange resin is gel-type.

(6)
The method for producing refined glycerin alkyl ether described in any one of (1) to (5), wherein the cation exchange resin is strong acid.

(7)
The method for producing refined glycerin alkyl ether described in any one of (1) to (6), wherein the degree of crosslinking of the cation exchange resin is preferably from 2 to 20%, more preferably from 4 to 16%, even more preferably from 6 to 10%.

(8)
The method for producing refined glycerin alkyl ether described in any one of (1) to (7), wherein the exchange capacity of the cation exchange resin is preferably from 0.5 meq/mL to 3.0 meq/mL, more preferably from 1.0 meq/mL to 2.5 meq/mL, even more preferably from 1.3 meq/mL to 1.8 meq/mL.

(9)
The method for producing refined glycerin alkyl ether described in any one of (1) to (8), wherein the water content of the solvent is preferably 5% by mass or less, more preferably 3% by mass or less, even more preferably 1% by mass or less.

(10)
The method for producing refined glycerin alkyl ether described in any one of (1) to (9), wherein the volume ratio (v/v) of the above-mentioned mixture/cation exchange resin, as the amount of the cation exchange resin to be used, is preferably 0.005 or more, more preferably 0.01 or more, even more preferably 0.03 or more, and is preferably 0.5 or less, more preferably 0.1 or less, even more preferably 0.05 or less.

(11)
The method for producing refined glycerin alkyl ether described in any one of (1) to (9), wherein the volume ratio (v/v) of the above-mentioned mixture/cation exchange resin, as the amount of the cation exchange resin to be used, is preferably from 0.005 to 0.5, more preferably from 0.01 to 0.1, even more preferably from 0.03 to 0.05.

(12)
The method for producing refined glycerin alkyl ether described in any one of (1) to (11), wherein the SP value of the solvent is preferably 23 $(MPa)^{1/2}$ or more, more preferably 24 $(MPa)^{1/2}$ or more, more preferably 25 $(MPa)^{1/2}$ or more, even more preferably 26 $(MPa)^{1/2}$ or more, and is preferably 33 $(MPa)^{1/2}$ or less, more preferably 32 $(MPa)^{1/2}$ or less, more preferably 31 $(MPa)^{1/2}$ or less, even more preferably 30 $(MPa)^{1/2}$ or less.

(13)
The method for producing refined glycerin alkyl ether described in any one of (1) to (11), wherein the SP value of the solvent is preferably from 23 to 33 $(MPa)^{1/2}$, more preferably from 24 to 32 $(MPa)^{1/2}$, more preferably from 25 to 31 $(MPa)^{1/2}$, even more preferably from 26 to 30 $(MPa)^{1/2}$.

(14)

The method for producing refined glycerin alkyl ether described in any one of (1) to (13), wherein the boiling temperature of the solvent at atmospheric pressure is preferably from 40 to 95° C., more preferably from 50 to 90° C., more preferably from 55 to 85° C., even more preferably from 60 to 80° C.

(15)

The method for producing refined glycerin alkyl ether described in any one of (1) to (14), wherein the mixture in step (1) contains a solvent which is the same as the solvent used in step (2).

(16)

The method for producing refined glycerin alkyl ether described in anyone of (1) to (15), wherein the solvent is at least one selected from methanol and ethanol.

(17)

The method for producing refined glycerin alkyl ether described in any one of (1) to (16), wherein the superficial velocity (SV) is preferably from 0.5 to 10/hr, more preferably from 2 to 4/hr, provided that the contact treatment with the cation exchange resin is the fixed bed method.

(18)

The method for producing refined glycerin alkyl ether described in any one of (1) to (17), wherein the superficial linear velocity is preferably from 0.2 to 4.9 m/h, more preferably from 1 to 2 m/h, provided that the contact treatment with the cation exchange resin in step (1) is the fixed bed method.

(19)

The method for producing refined glycerin alkyl ether described in any one of (1) to (18), wherein the contact temperature is preferably from 30 to 90° C., more preferably from 40 to 80° C., even more preferably from 50 to 65° C., provided that the contact treatment with the cation exchange resin in step (1) is the fixed bed method.

(20)

The method for producing refined glycerin alkyl ether described in any one of (1) to (19), wherein the superficial velocity (SV) is preferably from 0.5 to 10/hr, more preferably from 2 to 4/hr, provided that the contact treatment with the cation exchange resin in step (2) is the fixed bed method.

(21)

The method for producing refined glycerin alkyl ether described in any one of (1) to (20), wherein the superficial linear velocity is preferably from 0.2 to 4.9 m/h, more preferably from 1 to 2 m/h, provided that the contact treatment with the cation exchange resin in step (2) is the fixed bed method.

(22)

The method for producing refined glycerin alkyl ether described in any one of (1) to (21), wherein the contact temperature is preferably from 30 to 90° C., more preferably from 40 to 80° C., even more preferably from 50 to 65° C., provided that the contact treatment with the cation exchange resin in step (2) is the fixed bed method.

(23)

The method for producing refined glycerin alkyl ether described in any one of (1) to (22), wherein the amount of the solvent used relative to the above-mentioned mixture is preferably 2 or more, more preferably 5 or more, more preferably 10 or more, even more preferably 20 or more, and is preferably 200 or less, more preferably 180 or less, more preferably 160 or less, even more preferably 150 or less, provided that the contact treatment with the cation exchange resin in step (2) is the fixed bed method.

(24)

The method for producing refined glycerin alkyl ether described in any one of (1) to (22), wherein the amount of the solvent used relative to the above-mentioned mixture is preferably from 2 to 200, more preferably from 5 to 180, more preferably from 10 to 160, even more preferably from 20 to 150, provided that the contact treatment with the cation exchange resin in step (2) is the fixed bed method.

(25)

The method for producing refined glycerin alkyl ether described in any one of (1) to (16), wherein the steps (1) and (2) are performed according to the simulated moving bed chromatography.

(26)

The method for producing refined glycerin alkyl ether described in (25), wherein the ratio (Ud/Uf) of the feeding velocity of the solvent as the eluent (Ud) to the feeding velocity of the above-mentioned mixture as the raw material liquid (Uf) is preferably 2 or more, more preferably 3 or more, more preferably 3.5 or more, more preferably 4 or more, even more preferably 5 or more, and is preferably 40 or less, more preferably 25 or less, more preferably 20 or less, more preferably 18 or less, even more preferably 15 or less.

(27)

The method for producing refined glycerin alkyl ether described in (25), wherein the ratio (Ud/Uf) of the feeding velocity of the solvent (Ud) to the feeding velocity of the above-mentioned mixture (Uf) is preferably from 2 to 40, more preferably from 3 to 25, more preferably from 3.5 to 20, more preferably from 4 to 18, even more preferably from 5 to 15.

(28)

The method for producing refined glycerin alkyl ether described in (25) or (26), wherein the feeding velocity relative to the total column length (Uf) is preferably from 0.001 to 0.1 m/m/h, more preferably from 0.005 to 0.05 m/m/h, even more preferably from 0.01 to 0.03 m/m/h.

(29)

The method for producing refined glycerin alkyl ether described in any one of (25) to (28), wherein the total number of the columns is preferably from 8 to 16, more preferably from 10 to 14, even more preferably 12.

(30)

The method for producing refined glycerin alkyl ether described in any one of (25) to (29), wherein the number of the columns in each zone is preferably from 2 to 4 for zone 1, from 3 to 4 for zone 2, from 3 to 4 for zone 3, and from 3 to 4 for zone 4, more preferably 2 for zone 1, 4 for zone 2, 3 for zone 3, and 3 for zone 4, provided that the packed bed columns are composed of 4 zones.

(31)

The method for producing refined glycerin alkyl ether described in any one of (25) to (30), wherein the contact temperature is preferably from 30 to 90° C., more preferably from 40 to 80° C., even more preferably from 50 to 65° C.

(32)

The method for producing refined glycerin alkyl ether described in any one of (1) to (31), wherein the above-mentioned mixture contains a reaction product of glycerin and alkyl glycidyl ether or olefin.

(33)

The method for producing refined glycerin alkyl ether described in (32), wherein the feed amount of glycerin relative to one mole of alkyl glycidyl ether is preferably from 1 to 10 moles, more preferably from 1.2 to 7 moles, even more preferably from 2 to 6 moles.

(34)

The method for producing refined glycerin alkyl ether described in (32) or (33), wherein the content of glycerin alkyl ether in the reaction product is preferably from 5 to 60% by mass, more preferably from 10 to 50% by mass, even more preferably from 15 to 40% by mass.

(35)

The method for producing refined glycerin alkyl ether described in any one of (1) to (34), comprising a step to remove the solvent in the eluate obtained in step (2), after step (2).

(36)

The method for producing refined glycerin alkyl ether described in any one of (1) to (35), wherein the purity of refined glycerin alkyl ether is usually from 46 to 100% by mass, preferably from 50 to 99.8%, more preferably from 70 to 99.5%, more preferably from 75 to 99%, more preferably from 85 to 98.5%, even more preferably from 90 to 98%.

(37)

The method for producing refined glycerin alkyl ether described in any one of (1) to (36), wherein the recovery of refined glycerin alkyl ether is preferably from 80% to 100% by mass and the lower limit is more preferably 85% or more, more preferably 90% or more, even more preferably 95% or more.

EXAMPLES

1. Analysis of Glycerin and Glycerin Alkyl Ether

<Drying Condition>

The samples were dried for 3 hours in an electric constant temperature drier at 40° C. The dried residue was analyzed by gas chromatography (GC). When the sample amount was large or a high boiling point solvent was used, the samples were concentrated in a condition of 40° C./10 Torr by an evaporator, and directly dried for 3 hours in an electric constant temperature drier at 40° C. The dried residue was analyzed by gas chromatography (GC) or high performance liquid chromatography (HPLC).

<Analysis Method>

<Gas Chromatographic Analysis>

To the samples was added trimethylsilylation agent (TMSI-H) produced by GL Science Co. and mixed. After filtering out the solid fraction, the samples were quantitatively analyzed by GC under the following conditions.

GC Apparatus: HP6850 Series (produced by Hewlett Packard)

Column: D81-HT (produced by J&W, inner diameter 0.25 mm, length 15 m, membrane thickness 0.1 mm)

Carrier gas: He

Gas flow rate: 1.0 mL/min

Injection port temperature: 300° C.

Detector: FID type

Detector temperature: 300° C.

Column temperature condition: keep 60° C. for 2 minutes, then raise temperature at 10° C./min, keep 350° C.

<High Performance Liquid Chromatography (HPLC) Analysis>

To the samples was added acetonitrile/water and mixed. The samples were quantitatively analyzed by HPLC under the following conditions.

HPLC apparatus: Hitachi D-7000

Flow rate: 1.0 mL/min

Detector: Corona CAD detector produced by ESA Biosciences

<Analysis of Glycerin>

Column: TSK-GEL Amide-80, produced by Tosoh Corporation, 5 μm, 4.6×250 mm

Solution condition: 50 vol % acetonitrile/water (distilled)

<Analysis of Glycerin Alkyl Ether>

Column: Inertsil C8-3, produced by GL Science, 5 μm, 4.6×150 mm

Solution condition: acetonitrile/water (distilled)

Keep 45 vol % acetonitrile for 3 minutes, linear gradient from 45 to 98 vol % over 9 minutes, then keep 98 vol %

2. Measurement of Average Particle Diameter

A particle size distribution measuring apparatus based on laser diffraction scattering (LS 13 320, Beckman Coulter) was used to measure the average particle diameter of the cation exchange resin.

3. Measurement of Water Content

Water content of the samples was measured according to Karl Fischer coulometric titration, using the following apparatus and reagent.

Apparatus: Hiranuma AQ-300

Reagent: Aqualyte RO-A (produced by Hiranuma Sangyo Corporation)

Production Example 1

A reaction vessel was charged with 150 kg of lauryl alcohol (Produced by Kao Corporation) and 1.20 kg of lanthanum trifluoromethane sulfonate (produced by Tokyo Chemical Industry Co., Ltd.) and stirring was started. After raising the temperature up to 100° C., glycidol (produced by NOF Corporation) was dropped over 4.5 hours, followed by aging for 3 hours. After aging, 100 L of methanol (produced by Daisho Kasei Co., Ltd.) was added to form a solution. Then 100 L of ion exchange resin (Purolite MB378LT) was added and the mixture was stirred for 20 hours at room temperature. After removing the ion exchange resin by filtration, the temperature was raised up to 90° C. under a pressure of 4.0 to 5.3 kPa to remove methanol and obtain 238 kg of the raw material for distillation. Molecular distillation was performed for 231.7 kg of the material under the condition of 0.02 kPa to distill the unreacted lauryl alcohol and glycerin lauryl ether and to obtain 72.0 kg of the residue in the reaction vessel as "reaction product 1".

Then "reaction product 1" and diglycerin (produced by Tokyo Chemical Industry Co., Ltd.) were mixed so that the mass ratio of "reaction product 1" and diglycerin was 39.9/60.1. This mixture was used as "raw material 1". The composition of "raw material 1" is shown in Table 1.

Production Example 2

"Reaction product 1" and diglycerin (produced by Tokyo Chemical Industry Co., Ltd.) were mixed so that the mass ratio of "reaction product 1" and diglycerin was 32.1/67.9. This mixture was used as "raw material 2". The composition of "raw material 2" is shown in Table 1.

Production Example 3

Reaction Step (1)

A reaction vessel was charged with 500 kg of monoglycerin and 3.75 kg of potassium carbonate (produced by Wako Pure Chemical Industries, Ltd.) and stirring was started. After the pressure was reduced to 67 kPa, the temperature was raised to 240° C. Stirring was continued and monoglycerin was polymerized by maintaining the temperature and pressure for 8.5 hours, while removing water generated from the reaction.

Then 460 L of ion exchange water was added to the product to make an aqueous solution. To the aqueous solution was added 198 kg of ion exchange resin (Purolite MB378LT). The slurry was deionized by stirring for 5 hours, while keeping its temperature at 40° C.

The whole slurry was removed from the reaction vessel and the ion exchange resin was filtered out.

The filtrate was fed into the reaction vessel and water was removed from the filtrate at a temperature of 145° C. and a pressure of 0.47 kPa.

Then, the liquid temperature was raised up to 230° C. while keeping the pressure at 0.47 kPa to distill the component of glycerin with low degree of polymerization.

The pressure of the reaction vessel was reduced to 0.17 kPa and the liquid temperature was raised up to 260° C. to obtain the fraction containing diglycerin as the major component.

The residual component in the reaction vessel and the above-mentioned fraction were mixed and used for the reaction step (2) as glycerin.

Reaction Step (2)

A four neck flask was charged with 19.8 g of lauryl glycidyl ether and 121 g of glycerin all at once and the reaction was performed for 4 hours at 200° C., under nitrogen atmosphere and without catalyst to obtain "reaction product 2". The reaction product 2 was used as "raw material 3". The composition of "raw material 3" is shown in Table 1.

The amount of charged glycerin was 6 moles relative to one mole of alkyl glycidyl ether.

Production Example 4

"Reaction product 1" and glycerin #310 (produced by Sakamoto Yakuhin Kogyo Co., Ltd.) were mixed so that the mass ratio of "reaction product 1" and glycerin #310 was 32/68. This mixture was used as "raw material 4". The composition of "raw material 4" is shown in Table 1.

TABLE 1

|  | Degree of polymerization of glycerin (n) | Raw material 1 | Raw material 2 | Raw material 3 | Raw material 4 |
|---|---|---|---|---|---|
| Glycerin | 1 | — | — | 0.2 | 10.4 |
|  | 2 | 60.1 | 67.9 | 22.9 | 16.4 |
|  | 3 | — | — | 33.6 | 11.6 |
|  | 4 | — | — | 12.6 | 7.4 |
|  | 5 | — | — | 4.4 | 4.7 |
|  | 6 | — | — | 1.5 | 3.6 |
|  | 7 | — | — | 0.5 | 3.1 |
|  | 8 | — | — | 0.1 | 2.2 |
|  | Cyclic body | — | — | 0.6 | 8.5 |
| Glycerin monoalkyl ether | 1 | 0.5 | 0.4 | 0.4 | 0.6 |
|  | 2 | 13.9 | 11.2 | 0.1 | 13.8 |
|  | 3 | 10.7 | 8.6 | 5.4 | 6.6 |
|  | 4 | 6.4 | 5.2 | 8.4 | 4.2 |
|  | 5 | 4.0 | 3.2 | 3.5 | 2.7 |
|  | 6 or more | 4.4 | 3.5 | 1.7 | 4.2 |
| Glycerin dialkyl ether | 4 | — | — | 1.1 | — |
|  | 5 | — | — | 1.8 | — |
|  | 6 | — | — | 0.6 | — |
|  | 7 | — | — | 0.4 | — |
| Component 1: Glycerin with degree of polymerization 5 or less (%) | | 60.1 | 67.9 | 73.7 | 50.5 |
| Component 2: Glycerin with degree of polymerization 6 or more and cyclic body of glycerin (%) | | 0 | 0 | 2.7 | 17.4 |
| Component 3: Glycerin monoalkyl ether with degree of polymerization 5 or less (%) | | 35.5 | 28.6 | 17.8 | 27.9 |
| Component 4: Glycerin monoalkyl ether with degree of polymerization 6 or more (%) | | 4.4 | 3.5 | 1.7 | 4.2 |
| Component 5: Glycerin dialkyl ether (%) | | 0 | 0 | 4.1 | 0 |

Reference Examples 1 to 5

Confirmation of Dissolution

To 1 g of "Bond Elut Jr C18 produced by Varian Inc." was preliminarily passed 99.5% EtOH (2 mL) and then passed 30% EtOH (2 mL) twice for washing.

Then, "raw material liquid for dissolution evaluation", which was composed of 0.1606 g of "raw material 3" dissolved in 30% EtOH (2 mL), was passed to the preliminary washed "Bond Elut Jr C18" and the eluate was recovered by additionally passing 30% EtOH (2 mL) five times (Fr.1). Then, another eluate was recovered by passing 60% EtOH (2 mL) eight times (Fr.2). Finally, another eluate was recovered by passing 99.5% EtOH (4 mL) four times (Fr.3).

The solvent contained in "raw material liquid for dissolution evaluation" and its fractions, Fr.1, Fr.2, and Fr.3, was removed according to the drying condition in the aforementioned chromatographic analysis. The dissolution characteristics of the residues were evaluated upon contact again with the solvents listed in Table 2. The aforementioned chromatographic analysis of the "residues after solvent removal" of Fr.1, Fr.2 and Fr.3 of "raw material liquid for dissolution evaluation" revealed that "residue of Fr.1" contained component 1 (glycerin with degree of polymerization of 5 or less) and component 2 (glycerin with degree of polymerization of 6 or more and cyclic body of glycerin) only, "residue of Fr.2" contained component 3 (glycerin monoalkyl ether with degree of polymerization of 5 or less) and component 4 (glycerin monoalkyl ether with degree of polymerization of 6 or more) only, and "residue of Fr.3" contained component 5 (glycerin dialkyl ether) only.

Evaluation of Solubility

For evaluation, the solutions prepared by dissolving the residues again in predetermined solvents and adjusting the temperature to 50° C. were visually inspected. Amount of the solvent to be used was adjusted so that the concentration of the solvent was 50% by mass. The results are shown in Table 2.

Evaluation Criteria

Good: dissolved within 30 minutes (neither clouding nor phase separation observed)

Poor: not dissolved within 30 minutes (either clouding or phase separation observed)

TABLE 2

|  |  | Reference Example 1 | Reference Example 2 | Reference Example 3 | Reference Example 4 | Reference Example 5 |
|---|---|---|---|---|---|---|
| Solvent 1 | type | Acetone | Ethanol | Methanol | Ethanol | Ethanol |
|  | [wt %] | 100 | 100 | 100 | 60 | 30 |
| Solvent 2 | type | — | — | — | water | water |
|  | [wt %] | — | — | — | 40 | 70 |
| SP value of solvent | [MPa]$^{0.5}$ | 20.1 | 26.7 | 29.7 | 34.2 | 40.6 |
| Raw material 3 | Solubility | good | good | good | good | good |
| Residue after solvent removal of Fr. 1 of raw material for dissolution evaluation | Solubility | poor | good | good | good | good |
| Residue after solvent removal of Fr. 2 of raw material for dissolution evaluation | Solubility | good | good | good | good | poor |
| Residue after solvent removal of Fr. 3 of raw material for dissolution evaluation | Solubility | good | good | good | poor | poor |

Example 1

A column (inner diameter 10 mm, height 50 cm, void fraction 0.4) was filled with 39 mL of gel-type strong acid cation exchange resin having sodium ion as the counterion (average particle diameter 315 μm, AMBERLITE CR1310 Na, degree of crosslinking 6%, exchange capacity 1.5 meq/mL, produced by Dow Chemical Co.). Then, "raw material 1" was dissolved in methanol so that the content of the solvent in the mixture was 50% by mass and used as the raw material liquid. Methanol was used as the eluent. The SP value of methanol is 29.7 $(MPa)^{1/1}$. The raw material liquid was passed under the following conditions: superficial velocity 3.1/h, superficial linear velocity 1.53 m/h, contact temperature in the vessel 60° C., solvent temperature 65° C. After passing the raw material liquid for 50 seconds, the eluate at the outlet port of the column was collected every 2 minutes while passing the above-mentioned eluent for 119 minutes.

The volume ratio (v/v) of "raw material 1"/cation exchange resin was 0.042.

The amount of the solvent used relative to "raw material 1" (v/v) was 143.

The resultant eluate was subjected to gas chromatographic analysis to generate the chromatogram of each component. The solvent was completely volatilized by drying for 3 hours in an electric constant temperature drier at 40° C. Sample recovery for analysis was possible, since foaming did not occur even in concentration of the raw material liquid using an evaporator. Distribution coefficient K of each component was calculated from the analytical values obtained and is shown in Table 3. Note that the distribution coefficient K is a value obtained by dividing the amount adsorbed to the resin by the amount of each component eluted in the eluate and is indicative of good separation between the components when the distribution coefficient differs significantly for each component. Overall transfer coefficient Kfav of each component was also calculated and is shown in Table 4. In addition, composition in the simulated moving bed chromatographic separation was calculated using a chromatographic separation simulator (produced by Organo Corporation) under liquid passing conditions shown in Table 5.

Simulated Moving Bed Separation Apparatus Used in Chromatographic Separation Simulator A simulated moving bed separation apparatus shown in FIG. 1 was constructed by connecting 12 columns filled with the adsorbent used in the preliminary examination in series and endlessly so that zone 1 was composed of 2 columns, zone 2 was composed of 4 columns, zone 3 was composed of 3 columns and zone 4 was composed of 3 columns. Composition was calculated using a chromatographic separation simulator assuming that the separation apparatus was run under the conditions that the contact temperature in the vessel was 60° C. and the solvent temperature was 65° C. Liquid passing velocity in each zone was represented by U1 to U4, respectively.

The raw material liquid was passed to zone 2 and its feeding velocity was represented by Uf. The eluent was passed to zone 4 and its feeding velocity was represented by Ud.

A part of the liquid discharged from zone 2 was recovered as raffinate and the rest was passed to zone 1. Discharge velocity of the raffinate was represented by Ua. The raffinate fraction is rich in "component 3 (glycerin monoalkyl ether with degree of polymerization of 5 or less)", "component 4 (glycerin monoalkyl ether with degree of polymerization of 6 or more)", and "component 5 (glycerin dialkyl ether)".

A part of the liquid discharged from zone 4 was recovered as extract and the rest was passed to zone 3. Discharge velocity of the extract was represented by Uc. The extract fraction is rich in "component 1 (glycerin with degree of polymerization of 5 or less)" and "component 2 (glycerin with degree of polymerization of 6 or more and cyclic body of glycerin)".

In order to perform such operation continuously, calculation was performed to switch the positions of the feeding port of the raw material, the feeding port of the solvent, and each discharge port for every switching time Ts (hr).

Composition was calculated by keeping Uf, Ud/Uf, and time cycle constant and varying U1, U3, U4, Ud, and Uc arbitrarily. The calculation results are shown in Table 5.

Example 2

Chromatogram of each component was generated according to the similar operation to Example 1, using gel-type strong acid cation exchange resin having calcium ion as the counterion (average particle diameter 315 μm, AMBERLITE CR1310 Ca, degree of crosslinking 6%, exchange capacity 1.5 meq/mL, produced by Dow Chemical Co.). Composition in the simulated moving bed chromatographic separation was calculated using the distribution coefficient in Table 3 and overall mass transfer coefficient in Table 4 obtained from the chromatogram, according to the similar operation to Example 1, except that the operation conditions were changed to those shown in Table 5. The calculation result is shown in Table 5.

Example 3

Chromatogram of each component was generated according to the similar operation and analysis to Example 1, using a raw material liquid containing 15% by mass of the solvent in the mixture. Composition in the simulated moving bed chromatographic separation was calculated using the distribution coefficient in Table 3 and overall mass transfer coefficient in Table 4 obtained from the chromatogram, according to the similar operation to Example 1, except that the operation conditions were changed to those shown in Table 5. The calculation result is shown in Table 5.

Example 4

Chromatogram of each component was generated according to the similar operation and analysis to Example 1, using ethanol as the eluent. Composition in the simulated moving bed chromatographic separation was calculated using the distribution coefficient in Table 3 and overall mass transfer coefficient in Table 4 obtained from the chromatogram, according to the similar operation to Example 1, except that the operation conditions were changed to those shown in Table 5. The calculation result is shown in Table 5.

Example 5

Chromatogram of each component was generated according to the similar operation and analysis to Example 4, using gel-type strong acid cation exchange resin with the average particle diameter of 213 μm (UBK530, degree of crosslinking 6%, exchange capacity 1.6 meq/mL, produced by Mitsubishi Chemical Corporation). Composition in the simulated moving bed chromatographic separation was calculated using the distribution coefficient in Table 3 and overall mass transfer coefficient in Table 4 obtained from the chromatogram, according to the similar operation to Example 4, except that the operation conditions were changed to those shown in Table 5. The calculation result is shown in Table 5.

Example 6

Chromatogram of each component was generated according to the similar operation and analysis to Example 4, using gel-type strong acid cation exchange resin with the average particle diameter of 834 μm (SK104, degree of crosslinking 4%, exchange capacity 1.2 meq/mL, produced by Mitsubishi Chemical Corporation). Composition in the simulated moving bed chromatographic separation was calculated using the distribution coefficient in Table 3 and overall mass transfer coefficient in Table 4 obtained from the chromatogram, according to the similar operation to Example 4, except that the operation conditions were changed to those shown in Table 5. The calculation result is shown in Table 5.

Example 7

Chromatogram of each component was generated according to the similar operation and analysis to Example 4, using porous-type strong acid cation exchange resin with the average particle diameter of 834 μm (PK220, degree of crosslinking 10%, exchange capacity 1.9 meq/mL, produced by Mitsubishi Chemical Corporation). Composition in the simulated moving bed chromatographic separation was calculated using the distribution coefficient in Table 3 and overall mass transfer coefficient in Table 4 obtained from the chromatogram, according to the similar operation to Example 4, except that the operation conditions were changed to those shown in Table 5. The calculation result is shown in Table 5.

Comparative Example 1

The experiment was performed according to the similar operation to Example 3, except that distilled water was used as the eluent. Although the sample was dried for 3 hours in an electric constant temperature drier at 40° C. based on the drying condition in the aforementioned chromatographic analysis, the solvent did not volatilize. In addition, when the raw material liquid was concentrated using an evaporator, foaming occurred and recovery of the sample for analysis was difficult.

Comparative Example 2

The experiment was performed according to the similar operation to Example 3, except that a mixture of distilled water and ethanol (water content 7% by mass) was used as the eluent and that aromatic-based synthetic adsorbent with the average particle diameter of 303 μm (USP70, produced by Mitsubishi Chemical Corporation) was used. Although the sample was dried for 3 hours in an electric constant temperature drier at 40° C. based on the drying condition in the aforementioned chromatographic analysis, the solvent did not sufficiently volatilize. In addition, when the raw material liquid was concentrated using an evaporator, foaming occurred and recovery of the sample for analysis was difficult.

Comparative Example 3

Chromatogram of each component was generated according to the similar operation and analysis to Example 4, using aromatic-based synthetic adsorbent with the average particle diameter of 303 μm (USP70, produced by Mitsubishi Chemical Corporation) as the adsorbent. Composition in the simulated moving bed chromatographic separation was calculated using the distribution coefficient in Table 3 and overall mass transfer coefficient in Table 4 obtained from the chromatogram, according to the similar operation to Example 4, except that the operation conditions were changed to those shown in Table 5. The calculation result is shown in Table 5.

Comparative Example 4

Chromatogram of each component was generated according to the similar operation and analysis to Example 1, using silica gel with the average particle diameter of 263 μm (Silica Gel 4B, produced by Fuji Silysia Chemical Ltd.) as the adsorbent. Composition in the simulated moving bed chromatographic separation was calculated using the distribution coefficient in Table 3 and overall mass transfer coefficient in Table 4 obtained from the chromatogram, according to the similar operation to Example 1, except that the operation conditions were changed to those shown in Table 5. The calculation result is shown in Table 5.

TABLE 3

| | Degree of polymerization of glycerin (n) | Example 1 | Example 2 | Example 3 | Example 4 | Example 5 | Example 6 | Example 7 | Comparative example 1 | Comparative example 2 |
|---|---|---|---|---|---|---|---|---|---|---|
| Glycerin | 1 | — | — | — | — | — | — | — | — | — |
| | 2 | 0.82 | 1.06 | 1.12 | 1.15 | 1.34 | 0.21 | 4.25 | — | — |
| | 3 | — | — | — | — | — | — | — | — | — |
| | 4 | — | — | — | — | — | — | — | — | — |
| | 5 | — | — | — | — | — | — | — | — | — |
| | 6 | — | — | — | — | — | — | — | — | — |
| | 7 | — | — | — | — | — | — | — | — | — |
| | 8 | — | — | — | — | — | — | — | — | — |
| | Cyclic body | — | — | — | — | — | — | — | — | — |
| Glycerin monoalkyl ether | 1 | 0.23 | 0.11 | 1.61 | 1.83 | 2.15 | 1.89 | 3.40 | — | — |
| | 2 | 0.19 | 0.15 | 0.38 | 0.45 | 0.54 | 0.05 | 0.41 | — | — |
| | 3 | 0.20 | 0.16 | 0.39 | 0.46 | 0.56 | 0.06 | 0.43 | — | — |
| | 4 | 0.19 | 0.16 | 0.39 | 0.45 | 0.52 | 0.05 | 0.42 | — | — |
| | 5 | 0.19 | 0.16 | 0.34 | 0.45 | 0.53 | 0.05 | 0.37 | — | — |
| | 6 or more | 0.40 | 0.54 | 0.41 | 0.58 | 1.18 | 0.72 | 1.47 | — | — |
| Polyglycerin dialkyl ether | 4 | — | — | — | — | — | — | — | — | — |
| | 5 | — | — | — | — | — | — | — | — | — |
| | 6 | — | — | — | — | — | — | — | — | — |
| | 7 | — | — | — | — | — | — | — | — | — |
| Distribution coefficient K of component 1 (Glycerin with degree of polymerization 5 or less) and component 2 (Glycerin with degree of polymerization 6 or more and cyclic body of glycerin) | | 0.82 | 1.06 | 1.12 | 1.15 | 1.34 | 0.21 | 4.25 | — | — |
| Distribution coefficient K of component 3 (Glycerin monoalkyl ether with degree of polymerization 5 or less) | | 0.19 | 0.16 | 0.38 | 0.45 | 0.54 | 0.05 | 0.41 | — | — |
| Distribution coefficient K of component 4 (Glycerin monoalkyl ether with degree of polymerization 6 or more) | | 0.40 | 0.54 | 0.41 | 0.58 | 1.19 | 0.72 | 1.47 | — | — |
| Distribution coefficient K of component 5 (Glycerin dialkyl ether) | | — | — | — | — | — | — | — | — | — |

| | Degree of polymerization of glycerin (n) | Comparative example 3 | Comparative example 4 | Example 8 | Example 9 | Example 10 | Example 11 |
|---|---|---|---|---|---|---|---|
| Glycerin | 1 | — | — | — | — | 1.58 | 1.68 |
| | 2 | 1.17 | 0.57 | 1.12 | 1.15 | 1.23 | 1.30 |
| | 3 | — | — | — | — | 0.71 | 1.11 |
| | 4 | — | — | — | — | 0.49 | 0.95 |
| | 5 | — | — | — | — | 0.38 | 0.84 |
| | 6 | — | — | — | — | 0.17 | 0.74 |
| | 7 | — | — | — | — | 0.07 | 0.66 |
| | 8 | — | — | — | — | 0.05 | 0.59 |
| | Cyclic body | — | — | — | — | 0.81 | 0.54 |
| Glycerin monoalkyl ether | 1 | 1.92 | 1.64 | 1.61 | 1.63 | 0.06 | 1.34 |
| | 2 | 1.38 | 0.48 | 0.38 | 0.45 | 0.11 | 0.48 |
| | 3 | 1.37 | 0.47 | 0.39 | 0.46 | 0.04 | 0.45 |
| | 4 | 1.33 | 0.44 | 0.39 | 0.45 | 0.04 | 0.43 |
| | 5 | 1.30 | 0.42 | 0.34 | 0.45 | 0.04 | 0.39 |
| | 6 or more | 1.38 | 0.74 | 0.41 | 0.58 | 0.02 | 0.46 |
| Polyglycerin dialkyl ether | 4 | — | — | — | — | 0.02 | — |
| | 5 | — | — | — | — | 0.02 | — |
| | 6 | — | — | — | — | 0.03 | — |
| | 7 | — | — | — | — | 0.03 | — |
| Distribution coefficient K of component 1 (Glycerin with degree of polymerization 5 or less) and component 2 (Glycerin with degree of polymerization 6 or more and cyclic body of glycerin) | | 1.17 | 0.57 | 1.12 | 1.15 | 0.63 | 0.98 |
| Distribution coefficient K of component 3 (Glycerin monoalkyl ether with degree of polymerization 5 or less) | | 1.36 | 0.46 | 0.38 | 0.45 | 0.06 | 0.44 |
| Distribution coefficient K of component 4 (Glycerin monoalkyl ether with degree of polymerization 6 or more) | | 1.38 | 0.74 | 0.41 | 0.58 | 0.02 | 0.46 |

TABLE 3-continued

|  | | | | | | |
|---|---|---|---|---|---|---|
| Distribution coefficient K of component 5 (Glycerin dialkyl ether) | — | — | — | — | 0.03 | — |

TABLE 4

| | Degree of polymerization of glycerin (n) | Example 1 | Example 2 | Example 3 | Example 4 | Example 5 | Example 6 | Example 7 | Comparative example 1 | Comparative example 2 |
|---|---|---|---|---|---|---|---|---|---|---|
| Glycerin | 1 | — | — | — | — | — | — | — | — | — |
|  | 2 | 2.8 | 2.1 | 3.3 | 3.2 | 3.4 | 0.4 | 20.8 | — | — |
|  | 3 | — | — | — | — | — | — | — | — | — |
|  | 4 | — | — | — | — | — | — | — | — | — |
|  | 5 | — | — | — | — | — | — | — | — | — |
|  | 6 | — | — | — | — | — | — | — | — | — |
|  | 7 | — | — | — | — | — | — | — | — | — |
|  | 8 | — | — | — | — | — | — | — | — | — |
|  | Cyclic body | — | — | — | — | — | — | — | — | — |
| Glycerin monoalkyl ether | 1 | 2.3 | 1.0 | 2.8 | 3.3 | 4.9 | 3.4 | 8.8 | — | — |
|  | 2 | 1.4 | 1.0 | 1.9 | 3.0 | 3.6 | 0.2 | 0.8 | — | — |
|  | 3 | 1.4 | 1.0 | 2.0 | 3.0 | 4.0 | 0.2 | 0.8 | — | — |
|  | 4 | 1.6 | 1.4 | 2.0 | 3.6 | 3.9 | 0.2 | 0.8 | — | — |
|  | 5 | 1.7 | 1.6 | 2.9 | 3.9 | 5.6 | 0.2 | 0.8 | — | — |
|  | 6 or more | 0.8 | 1.0 | 1.8 | 2.2 | 2.7 | 1.0 | 2.0 | — | — |
| Polyglycerin dialkyl ether | 4 | — | — | — | — | — | — | — | — | — |
|  | 5 | — | — | — | — | — | — | — | — | — |
|  | 6 | — | — | — | — | — | — | — | — | — |
|  | 7 | — | — | — | — | — | — | — | — | — |
| Mass transfer coefficient Kfav (1/hr) of component 1 (Glycerin with degree of polymerization 5 or less) and component 2 (Glycerin with degree of polymerization 6 or more and cyclic body of glycerin) | | 2.8 | 2.1 | 3.3 | 3.2 | 3.4 | 0.4 | 20.8 | — | — |
| Mass transfer coefficient Kfav (1/hr) of component 3 (Glycerin monoalkyl ether with degree of polymerization 5 or less) | | 1.5 | 1.2 | 2.2 | 3.4 | 4.3 | 0.2 | 0.9 | — | — |
| Mass transfer coefficient Kfav (1/hr) of component 4 (Glycerin monoalkyl ether with degree of polymerization 6 or more) | | 0.8 | 1.0 | 1.8 | 2.2 | 2.7 | 1.0 | 2.0 | — | — |
| Mass transfer coefficient Kfav (1/hr) of component 5 (Glycerin dialkyl ether) | | — | — | — | — | — | — | — | — | — |

| | | Degree of polymerization of glycerin (n) | Comparative example 3 | Comparative example 4 | Example 8 | Example 9 | Example 10 | Example 11 |
|---|---|---|---|---|---|---|---|---|
| | Glycerin | 1 | — | — | — | — | 3.9 | 5.1 |
| | | 2 | 11.5 | 10.8 | 3.3 | 3.2 | 2.9 | 3.0 |
| | | 3 | — | — | — | — | 1.6 | 2.4 |
| | | 4 | — | — | — | — | 1.1 | 2.4 |
| | | 5 | — | — | — | — | 0.8 | 2.4 |
| | | 6 | — | — | — | — | 0.9 | 2.4 |
| | | 7 | — | — | — | — | 0.8 | 2.4 |
| | | 8 | — | — | — | — | 0.7 | 2.4 |
| | | Cyclic body | — | — | — | — | 2.0 | 1.8 |
| | Glycerin monoalkyl ether | 1 | 6.3 | 3.5 | 2.8 | 3.3 | 0.5 | 2.7 |
| | | 2 | 15.4 | 6.5 | 1.9 | 3.0 | 1.0 | 1.6 |
| | | 3 | 14.3 | 5.9 | 2.0 | 3.0 | 0.3 | 1.6 |
| | | 4 | 14.0 | 14.6 | 2.0 | 3.6 | 0.3 | 1.6 |
| | | 5 | 13.7 | 22.1 | 2.9 | 3.9 | 0.3 | 1.7 |
| | | 6 or more | 11.3 | 1.9 | 1.8 | 2.2 | 0.1 | 2.6 |
| | Polyglycerin dialkyl ether | 4 | — | — | — | — | 0.2 | — |
| | | 5 | — | — | — | — | 0.2 | — |
| | | 6 | — | — | — | — | 0.3 | — |
| | | 7 | — | — | — | — | 0.4 | — |
| | Mass transfer coefficient Kfav (1/hr) of component 1 (Glycerin with degree of polymerization 5 or less) and component 2 (Glycerin with degree of polymerization 6 | | 11.5 | 10.8 | 3.3 | 3.2 | 1.7 | 2.8 |

TABLE 4-continued

|  |  |  |  |  |  |  |
|---|---|---|---|---|---|---|
| or more and cyclic body of glycerin) | | | | | | |
| Mass transfer coefficient Kfav (1/hr) of component 3 (Glycerin monoalkyl ether with degree of polymerization 5 or less) | 14.4 | 12.3 | 2.2 | 3.4 | 0.5 | 1.6 |
| Mass transfer coefficient Kfav (1/hr) of component 4 (Glycerin monoalkyl ether with degree of polymerization 6 or more) | 11.3 | 1.9 | 1.8 | 2.2 | 0.1 | 2.6 |
| Mass transfer coefficient Kfav (1/hr) of component 5 (Glycerin dialkyl ether) | — | — | — | — | 0.2 | — |

TABLE 5

|  |  |  | Example 1 | Example 2 | Example 3 | Example 4 | Example 5 | Example 6 |
|---|---|---|---|---|---|---|---|---|
| Raw material | Type of raw material | — | Raw material 1 | Raw material 1 | Raw material 1 | Raw material 1 | Raw material 1 | Raw material 1 |
| | Content of solvent in mixture | [wt %] | 50 | 50 | 15 | 15 | 15 | 15 |
| | Type of solvent | — | Methanol | Methanol | Methanol | Ethanol | Ethanol | Ethanol |
| | SP value of solvent | $[MPa]^{0.5}$ | 29.7 | 29.7 | 29.7 | 26.7 | 26.7 | 26.7 |
| | Water content of solvent | [wt %] | 0.1 | 0.1 | 0.1 | 1.1 | 1.1 | 1.1 |
| | Proportion of component 1 (Glycerin with degree of polymerization 5 or less) and component 2 (Glycerin with degree of polymerization 6 or more and cyclic body of glycerin) | [%] | 60.1 | 60.1 | 60.1 | 60.1 | 60.1 | 60.1 |
| | Proportion of component 3 (Glycerin monoalkyl ether with degree of polymerization 5 or less), component 4 (Glycerin monoalkyl ether with degree of polymerization 6 or more0) and component 5 (Glycerin dialkyl ether) | [%] | 39.9 | 39.9 | 39.9 | 39.9 | 39.9 | 39.9 |
| Separation conditions | Type of adsorbant | — | Strong acid cation exchange resin | Strong acid cation exchange resin | Strong acid cation exchange resin | Strong acid cation exchange resin | Strong acid cation exchange resin | Strong acid cation exchange resin |
| | Name of adsorbant | — | CR1310Na | CR1310Na | CR1310Na | CR1310Na | UBK530 | SK104 |
| | Average particle diameter of adsorbant | [μm] | 315 | 315 | 315 | 315 | 213 | 834 |
| | Functional group of cation exchange resin | — | Na | Ca | Na | Na | Na | Na |
| | Structure of cation exchange resin | — | Gel | Gel | Gel | Gel | Gel | Gel |
| | Type o solvent | — | Methanol | Methanol | Methanol | Ethanol | Ethanol | Ethanol |
| | SP value of solvent | $[MPa]^{0.5}$ | 29.7 | 29.7 | 29.7 | 26.7 | 26.7 | 26.7 |
| Recovery of separated liquid | Possibility of solvent distillation after separation | — | Good, no foaming | Good, no foaming | Good, no foaming | Good, no foaming | Good, no foaming | Good, no foaming |
| Operation conditions | U1 | [m/h] | 1.35 | 1.08 | 1.60 | 1.79 | 1.90 | 1.25 |
| | U2 | [m/h] | 2.60 | 2.85 | 2.60 | 2.92 | 2.90 | 1.94 |
| | U3 | [m/h] | 2.00 | 2.25 | 2.00 | 2.32 | 2.30 | 1.34 |
| | U4 | [m/h] | 3.55 | 3.28 | 3.80 | 3.99 | 4.10 | 3.45 |
| | Uf | [m/h] | 0.60 | 0.60 | 0.60 | 0.60 | 0.60 | 0.60 |
| | Ud | [m/h] | 2.20 | 2.20 | 2.20 | 2.20 | 2.20 | 2.20 |
| | Ua | [m/h] | 1.25 | 1.77 | 1.00 | 1.13 | 1.00 | 0.68 |
| | Uc | [m/h] | 1.55 | 1.03 | 1.80 | 1.67 | 1.80 | 2.12 |
| | Ts | [h] | 0.64 | 0.64 | 0.64 | 0.64 | 0.64 | 0.64 |
| Run conditions | Total column length | [m] | 23.4 | 23.4 | 23.4 | 23.4 | 23.4 | 23.4 |
| | column diameter | [m] | 1.0 | 1.0 | 1.0 | 1.0 | 1.0 | 1.0 |
| | column volume | [m³] | 18.4 | 18.4 | 18.4 | 18.4 | 18.4 | 18.4 |
| | Feeding velocity of raw material | [m/h] | 0.60 | 0.60 | 0.60 | 0.60 | 0.60 | 0.60 |
| | Ud/Uf | [—] | 3.7 | 3.7 | 3.7 | 3.7 | 3.7 | 3.7 |
| | Uf/Total column length | [m//m/h] | 0.026 | 0.026 | 0.026 | 0.026 | 0.026 | 0.026 |
| | Time cycle | [h] | 7.7 | 7.7 | 7.7 | 7.7 | 7.7 | 7.7 |

TABLE 5-continued

| Raffinate fraction | | | | | | | | |
|---|---|---|---|---|---|---|---|---|
| | Proportion of component 1 (Glycerin with degree of polymerization 5 or less) and component 2 (Glycerin with degree of polymerization 6 or more and cyclic body of glycerin) | [%] | 10 | 28 | 5 | 9 | 9 | 49 |
| | Proportion of component 3 (Glycerin monoalkyl ether with degree of polymerization 5 or less), component 4 (Glycerin monoalkyl ether with degree of polymerization 6 or more) | [%] | 90 | 72 | 95 | 91 | 91 | 51 |
| | Yield of component 3 (Glycerin monoalkyl ether with degree of polymerization 5 or less), component 4 (Glycerin monoalkyl ether with degree of polymerization 6 or more) and component 5 (Glycerin dialkyl ether) | [%] | 99 | 99 | 95 | 98 | 92 | 87 |

| | | | | Example 7 | Comparative example 1 | Comparative example 2 | Comparative example 3 | Comparative example 4 |
|---|---|---|---|---|---|---|---|---|
| Raw material | Type of raw material | | — | Raw material 1 | Raw material 1 | Raw material 1 | Raw material 1 | Raw material 1 |
| | Content of solvent in mixture | | [wt %] | 15 | 15 | 15 | 15 | 15 |
| | Type of solvent | | — | Ethanol | Distilled water | Distilled water/Ethanol | Ethanol | Methanol |
| | SP value of solvent | | [MPa]$^{0.5}$ | 26.7 | 48 | 27.8 | 26.7 | 29.7 |
| | Water content of solvent | | [wt %] | 1.1 | 100 | 7 | 1.1 | 0.1 |
| | Proportion of component 1 (Glycerin with degree of polymerization 5 or less) and component 2 (Glycerin with degree of polymerization 6 or more and cyclic body of glycerin) | | [%] | 60.1 | 60.1 | 60.1 | 60.1 | 60.1 |
| | Proportion of component 3 (Glycerin monoalkyl ether with degree of polymerization 5 or less), component 4 (Glycerin monoalkyl ether with degree of polymerization 6 or more) and component 5 (Glycerin dialkyl ether) | | [%] | 39.9 | 39.9 | 39.9 | 39.9 | 39.9 |
| Separation conditions | Type of adsorbant | | — | Strong acid cation exchange resin | Strong acid cation exchange resin | Synthetic adsorbent | Synthetic adsorbent | Silica gel |
| | Name of adsorbant | | — | PK220 | CR1310Na | USP70 | USP70 | Silica gel 4B |
| | Average particle diameter of adsorbant | | [μm] | 834 | 315 | 303 | 303 | 263 |
| | Functional group of cation exchange resin | | — | Na | Na | — | — | — |
| | Structure of cation exchange resin | | — | Porous | Gel | — | — | — |
| | Type o solvent | | — | Ethanol | Distilled water | Distilled water/Ethanol | Ethanol | Methanol |
| | SP value of solvent | | [MPa]$^{0.5}$ | 26.7 | 48 | 27.8 | 26.7 | 29.7 |
| Recovery of separated liquid | Possibility of solvent distillation after separation | | — | Good, no foaming | Considerable foaming, recovery impossible | Considerable foaming, recovery impossible | Good, no foaming | Good, no foaming |
| Operation conditions | U1 | | [m/h] | 0.67 | | | 3.11 | 1.94 |
| | U2 | | [m/h] | 2.64 | | | 4.03 | 2.70 |
| | U3 | | [m/h] | 2.04 | | | 3.43 | 2.10 |

TABLE 5-continued

| | | | | | |
|---|---|---|---|---|---|
| | U4 | [m/h] | 2.87 | 5.31 | 4.14 |
| | Uf | [m/h] | 0.60 | 0.60 | 0.60 |
| | Ud | [m/h] | 2.20 | 2.20 | 2.20 |
| | Ua | [m/h] | 1.97 | 0.92 | 0.76 |
| | Uc | [m/h] | 0.83 | 1.56 | 2.04 |
| | Ts | [h] | 0.64 | 0.64 | 0.64 |
| Run conditions | Total column length | [m] | 23.4 | 23.4 | 23.4 |
| | column diameter | [m] | 1.0 | 1.0 | 1.0 |
| | column volume | [m3] | 18.4 | 18.4 | 18.4 |
| | Feeding velocity of raw material (Uf) | [m/h] | 0.60 | 0.60 | 0.60 |
| | Ud/Uf | [—] | 3.7 | 3.7 | 3.7 |
| | Uf/Total column length | [m//m/h] | 0.026 | 0.026 | 0.026 |
| | Time cycle | [h] | 7.7 | 7.7 | 7.7 |
| Raffinate fraction | Proportion of component 1 (Glycerin with degree of polymerization 5 or less) and component 2 (Glycerin with degree of polymerization 6 or more and cyclic body of glycerin) | [%] | 54 | 72 | 55 |
| | Proportion of component 3 (Glycerin monoalkyl ether with degree of polymerization 5 or less), component 4 (Glycerin monoalkyl ether with degree of polymerization 6 or more) | [%] | 46 | 28 | 45 |
| | Yield of component 3 (Glycerin monoalkyl ether with degree of polymerization 5 or less), component 4 (Glycerin monoalkyl ether with degree of polymerization 6 or more) and component 5 (Glycerin dialkyl ether) | [%] | 86 | 53 | 88 |

The values of the distribution coefficient in Table 3 indicated that component 1 (glycerin with degree of polymerization of 5 or less) and component 2 (glycerin with degree of polymerization of 6 or more and cyclic body of glycerin) are strongly adsorbed by the resin and that component 3 (glycerin monoalkyl ether with degree of polymerization of 5 or less), component 4 (glycerin monoalkyl ether with degree of polymerization of 6 or more), and component 5 (glycerin dialkyl ether) are distributed to the eluate by using cation exchange resin as the adsorbent and a solvent with the SP value of from 20.5 to 34 $(MPa)^{1/2}$ as the eluent, showing that the present invention exerts high separation performance. In addition, data in Table 5 showed that glycerin alkyl ether can be recovered with high yield by using cation exchange resin as the adsorbent.

Example 8

Chromatogram of each component was generated according to the similar operation and analysis to Example 3, using "raw material 2" as the raw material liquid. Composition in the simulated moving bed chromatographic separation was calculated using the distribution coefficient in Table 3 and overall mass transfer coefficient in Table 4 obtained from the chromatogram, according to the similar operation to Example 3, except that the operation conditions were changed to those shown in Table 6. The calculation result is shown in Table 6.

Example 9

Chromatogram of each component was generated according to the similar operation and analysis to Example 4, using "raw material 2" as the raw material liquid. Composition in the simulated moving bed chromatographic separation was calculated using the distribution coefficient in Table 3 and overall mass transfer coefficient in Table 4 obtained from the chromatogram, according to the similar operation to Example 4, except that the operation conditions were changed to those shown in Table 6. The calculation result is shown in Table 6.

Example 10

The eluate obtained according to the similar operation to Example 1 using "raw material 3" as the raw material liquid was subjected to high performance liquid chromatography to generate the chromatogram of each component. Composition in the simulated moving bed chromatographic separation was calculated using the distribution coefficient in Table 3 and overall mass transfer coefficient in Table 4 obtained from the chromatogram, according to the similar operation to Example 1, except that the operation conditions were changed to those shown in Table 6. The calculation result is shown in Table 6.

Example 11

The eluate obtained according to the similar operation to Example 3 using "raw material 4" as the raw material liquid was subjected to high performance liquid chromatography to generate the chromatogram of each component. Composition in the simulated moving bed chromatographic separation was calculated using the distribution coefficient in Table 3 and overall mass transfer coefficient in Table 4 obtained from the chromatogram, according to the similar operation to Example 3, except that the operation conditions were changed to those shown in Table 6. The calculation result is shown in Table 6.

TABLE 6

| | | | Example 8 | Example 9 | Example 10 | Example 11 |
|---|---|---|---|---|---|---|
| Raw material | Type of raw material | — | Raw material 2 | Raw material 2 | Raw material 3 | Raw material 4 |
| | Content of solvent in mixture | [wt %] | 15 | 15 | 50 | 15 |
| | Type of solvent | — | Methanol | Ethanol | Methanol | Methanol |
| | SP value of solvent | [MPa]$^{0.5}$ | 29.7 | 26.7 | 29.7 | 29.7 |
| | Water content of solvent | [wt %] | 0.1 | 1.1 | 0.1 | 0.1 |
| | Proportion of component 1 (Glycerin with degree of polymerization 5 or less) and component 2 (Glycerin with degree of polymerization 6 or more and cyclic body of glycerin) | [%] | 67.9 | 67.9 | 76.4 | 67.9 |
| | Yield of component 3 (Glycerin monoalkyl ether with degree of polymerization 5 or less), component 4 (Glycerin monoalkyl ether with degree of polymerization 6 or more) and component 5 (Glycerin dialkyl ether) | [%] | 32.1 | 32.1 | 23.6 | 32.1 |
| Separation conditions | Type of adsorbant | — | Strong acid cation exchange resin | Strong acid cation exchange resin | Strong acid cation exchange resin | Strong acid cation exchange resin |
| | Name of adsorbant | — | CR1310Na | CR1310Na | CR1310Na | CR1310Na |
| | Average particle diameter of adsorbant | [μm] | 315 | 315 | 315 | 315 |
| | Functional group of cation exchange resin | — | Na | Na | Na | Na |
| | Structure of cation exchange resin | — | Gel | Gel | Gel | Gel |
| | Type of solvent | — | Methanol | Ethanol | Methanol | Methanol |
| | SP value of solvent | [MPa]$^{0.5}$ | 29.7 | 26.7 | 29.7 | 29.7 |
| Recovery of separated liquid | Possibility of solvent distillation after separation | — | Good, no foaming | Good, no foaming | Good, no foaming | Good, no foaming |
| Operation conditions | U1 | [m/h] | 1.58 | 1.79 | 0.33 | 1.39 |
| | U2 | [m/h] | 2.62 | 2.92 | 1.16 | 2.46 |
| | U3 | [m/h] | 2.02 | 2.32 | 0.80 | 2.10 |
| | U4 | [m/h] | 3.58 | 4.24 | 3.81 | 4.99 |
| | Uf | [m/h] | 0.60 | 0.60 | 0.36 | 0.36 |
| | Ud | [m/h] | 2.00 | 2.45 | 3.48 | 3.60 |
| | Ua | [m/h] | 1.04 | 1.13 | 0.83 | 1.07 |
| | Uc | [m/h] | 1.56 | 1.92 | 3.01 | 2.89 |
| | Ts | [h] | 0.64 | 0.64 | 0.87 | 0.64 |
| Run conditions | Total column length | [m] | 23.4 | 23.4 | 23.4 | 23.4 |
| | Column diameter | [m] | 1.0 | 1.0 | 1.0 | 1.0 |
| | Column volume | [m3] | 18.4 | 18.4 | 18.4 | 18.4 |
| | Feeding velocity of raw material (Uf) | [m/h] | 0.60 | 0.60 | 0.36 | 0.36 |
| | Ud/Uf | [—] | 3.3 | 4.1 | 10 | 10 |
| | Uf/Total column length | [m//m/h] | 0.026 | 0.026 | 0.015 | 0.015 |
| | Time cycle | [h] | 7.7 | 7.7 | 10.5 | 7.7 |
| Raffinate fraction | Proportion of component 1 (Glycerin with degree of polymerization 5 or less) and component 2 (Glycerin with degree of polymerization 6 or more and cyclic body of glycerin) | [%] | 10 | 10 | 10 | 23 |
| | Proportion of component 3 (Glycerin monoalkyl ether with degree of polymerization 5 or less), component 4 (Glycerin monoalkyl ether with degree of polymerization 6 or more) | [%] | 90 | 90 | 90 | 77 |
| | Yield of component 3 (Glycerin monoalkyl ether with degree of polymerization 5 or less), component 4 | [%] | 97 | 98 | 100 | 86 |

TABLE 6-continued

|  | Example 8 | Example 9 | Example 10 | Example 11 |
|---|---|---|---|---|
| (Glycerin monoalkyl ether with degree of polymerization 6 or more) and component 5 (Glycerin dialkyl ether) | | | | |

Data in Table 6 showed that the recovery and purity of glycerin alkyl ether decreases when the proportion of glycerin and cyclic body of glycerin in the raw material liquid increases.

The invention claimed is:

1. A method for producing refined glycerin alkyl ether comprising the following steps (1) and (2):
   step (1): bringing a mixture containing glycerin and glycerin alkyl ether into contact with a cation exchange resin;
   step (2): bringing the cation exchange resin into contact with a solvent having an SP value of from 20.5 to 34 $(MPa)^{1/2}$ to obtain an eluate, wherein the water content of the solvent is 5% by mass or less.

2. The method for producing refined glycerin alkyl ether according to claim 1, wherein the average particle diameter of the cation exchange resin is from 100 to 900 μm.

3. The method for producing refined glycerin alkyl ether according to claim 1, wherein the cation exchange resin is at least one selected from alkali metal type and alkali earth metal type.

4. The method for producing refined glycerin alkyl ether according to claim 1, wherein the cation exchange resin is gel-type.

5. The method for producing refined glycerin alkyl ether according to claim 1, wherein the cation exchange resin is strong acid.

6. The method for producing refined glycerin alkyl ether according to claim 1, wherein the degree of crosslinking of the cation exchange resin is from 2 to 20%.

7. The method for producing refined glycerin alkyl ether according to claim 1, wherein the exchange capacity of the cation exchange resin is from 0.5 meq/mL to 3.0 meq/mL.

8. The method for producing refined glycerin alkyl ether according to claim 1, wherein the volume ratio (v/v) of the above-mentioned mixture/cation exchange resin, as the amount of the cation exchange resin to be used, is from 0.005 to 0.5.

9. The method for producing refined glycerin alkyl ether according to claim 1, wherein the SP value of the solvent is from 23 to 33 $(MPa)^{1/2}$.

10. The method for producing refined glycerin alkyl ether according to claim 1, wherein the mixture in step (1) contains a solvent which is the same as the solvent used in step (2).

11. The method for producing refined glycerin alkyl ether according to claim 1, wherein the solvent is at least one selected from methanol and ethanol.

12. The method for producing refined glycerin alkyl ether according to claim 1, wherein the steps (1) and (2) are performed according to the simulated moving bed chromatography.

13. The method for producing refined glycerin alkyl ether according to claim 12, wherein the ratio (Ud/Uf) of the feeding velocity of the solvent (Ud) to the feeding velocity of the above-mentioned mixture (Uf) is from 2 to 40 mass fold.

14. The method for producing refined glycerin alkyl according to claim 12, wherein the feeding velocity relative to the total column length (Uf) is from 0.001 to 0.1 [m/m/h].

15. The method for producing refined glycerin alkyl ether according to claim 1, wherein the above-mentioned mixture contains a reaction product of glycerin and alkyl glycidyl ether or olefin.

16. The method for producing refined glycerin alkyl ether described in claim 15, wherein the feed amount of glycerin relative to one mole of alkyl glycidyl ether is from 1 to 10 moles.

17. The method for producing refined glycerin alkyl ether according to claim 1, wherein the content of glycerin alkyl ether in the mixture is from 5 to 60% by mass.

18. The method for producing refined glycerin alkyl ether according to claim 1, comprising a step to remove the solvent in the eluate obtained in step (2), after step (2).

19. The method for producing refined glycerin alkyl ether according to claim 1, wherein the purity of refined glycerin alkyl ether is from 46 to 100% by mass.

* * * * *